United States Patent [19]

Kao et al.

[11] 4,124,635

[45] Nov. 7, 1978

[54] PROCESS FOR THE LIQUID PHASE OXIDATION OF α,β-UNSATURATED ALDEHYDES TO α,β-UNSATURATED ACIDS USING ZINC CATALYSTS

[75] Inventors: Jar-lin Kao, Cherry Hill, N.J.; John J. Leonard, Springfield, Pa.

[73] Assignee: Atlantic Richfield Company, Los Angeles, Calif.

[21] Appl. No.: 774,845

[22] Filed: Mar. 7, 1977

[51] Int. Cl.$^2$ ............................................. C07C 51/32
[52] U.S. Cl. ..................................... 562/533; 562/598
[58] Field of Search ........... 260/530 N, 526 N, 539 R

[56] References Cited

U.S. PATENT DOCUMENTS 2,212,900   8/1940   Groll et al. ...................... 260/530 N

FOREIGN PATENT DOCUMENTS 4,018,287   8/1965   Japan .................................. 260/530 N
373,326     5/1932   United Kingdom ................ 260/530 N Primary Examiner—Vivian Garner
Attorney, Agent, or Firm—Delbert E. McCaslin

[57] ABSTRACT

A process for the liquid phase oxidation of α,β-unsaturated aliphatic aldehydes, such as methacrolein and the in situ decomposition or conversion of unsaturated peroxy (peroxide) compounds formed during the oxidation to the corresponding α,β-unsaturated aliphatic carboxylic acids which comprises passing oxygen or an oxygen-containing gas such as air through an inert solvent solution of the unsaturated aldehyde at a suitable temperature and pressure in the presence of an organic or inorganic zinc salt catalyst.

10 Claims, No Drawings

PROCESS FOR THE LIQUID PHASE OXIDATION OF α,β-UNSATURATED ALDEHYDES TO α,β-UNSATURATED ACIDS USING ZINC CATALYSTS

BACKGROUND OF THE INVENTION

A number of prior art processes have been proposed for the preparation of unsaturated carboxylic acids from their corresponding unsaturated aldehydes. Various catalytic vapor phase processes have been described employing complex catalyst systems. Liquid phase reactions include the use of hydroperoxides, molecular oxygen including air in the presence of various solvents and various organic and inorganic metal compounds of silver, nickel, cobalt, manganese, copper, chromium and vanadium used singly, in combination and with other materials such as bromine compounds and chelates. Generally the production of unsaturated aliphatic aldehydes in the liquid phase has been difficult due to polymerization of the unsaturated acids when formed and the co-production of various undesirable peroxides of the unsaturated acids and aldehydes formed during oxidation, resulting in low selectivity to and yield of the unsaturated acids.

To date no commercially successful process has been developed for the liquid phase preparation of unsaturated carboxylic acids, such as methacrylic acid, involving the in situ decomposition of the undesirable peroxidic by products formed during the autoxidation of the aldehyde such as methacrolein. None of the above noted prior art catalysts successfully decompose the peroxidic compounds in situ. The present process is directed to an improved process for the preparation of unsaturated carboxylic acids in high yields and avoiding problems associated with the prior art processes. More particularly, the process relates to the synthesis of unsaturated carboxylic acids by the liquid phase solvent solution oxidation of the corresponding unsaturated aldehyde and the in situ conversion (decomposition) of unsaturated peroxide compounds formed during said oxidation, by reacting the unsaturated aldehyde, and oxygen in a suitable solvent or mixture of solvents under moderate temperature and pressure conditions in the presence of a catalytic quantity of a zinc salt compound.

U.S. Pat. No. 3,114,769 in an attempt to prevent polymeric by-products, describes a liquid phase process for the oxidation of methacrolein or acrolein to the corresponding acid and peroxide compounds in the presence of molecular oxygen and a small quantity of iodine. The products of the oxidation contained mixtures of unsaturated acids, and large amounts of both acid and aldehyde peroxides and unreacted aldehydes. After separation the peroxide products were separately decomposed to the acid by the catalytic effect of a protonic acid such as p-toluene sulfonic acid and an alcohol forming a hot solvent solution as is further described in U.S. Pat. No. 3,253,025.

In an article by William F. Brill and Fred Lister, Journal of Organic Chemistry, Vol. 26, pp. 565–569, 1961 the metal-salt catalyzed oxidation of methacrolein in acetic acid is described. The methacrolein goes to peroxide products, acid and major amounts of soluble polymer.

The α,β-unsaturated acid products obtained by the process of this invention have many known commercial uses, particularly for the preparation of esters such as methyl methacrylate or methyl acrylate and as monomers for polymer formation.

A particular advantage of the process of the present invention is the discovery that catalyatic amounts of organic and inorganic zinc salt compounds permit the intermediate peroxy compounds formed during oxidation of the unsaturated aldehydes, e.g., permethacrylic acid and methacrolein monopermethacrylate, which are formed during oxidation of methacrolein, to decompose or be converted to methacrylic acid or in the case of other aldehydes the corresponding acids, and thus substantially increase selectivity to and yield of the particular unsaturated acid. Another advantage is that only small amounts of the zinc compounds need be employed and much less peroxy (peroxide) compounds which would otherwise be formed need be removed from the reaction product and further processed thus providing a commercially attractive liquid phase process.

SUMMARY OF THE INVENTION

In accordance with the present invention, there is provided an improved process for the liquid phase oxidation of α,β-unsaturated aliphatic aldehydes to the corresponding α,β-unsaturated aliphatic carboxylic acids in high yield by reacting the unsaturated aldehyde with oxygen in a suitable inert solvent, which process is carried out at relatively moderate temperatures and pressures in the presence of a catalytic amount of a zinc salt catalyst compound or mixtures thereof, which promote the decomposition or conversion of intermediate peroxides formed by the oxidation, to provide a pronounced effect on selectivity to and yield of unsaturated acid as compared to known liquid phase processes.

It is a primary object of this invention to provide an improved process for the liquid phase preparation of α,β-unsaturated aliphatic acids, such as methacrylic acid in high yield while avoiding operational problems associated with prior liquid phase processes for the oxidation of α, β-unsaturated lower aliphatic aldehydes.

It is another object of this invention to provide a novel reaction system useful for the in situ decomposition of co-produced peroxide compounds to the desired α, β-unsaturated acid, thereby preventing a build up of peroxide compounds during the autoxidation of the aldehyde.

It is a further object of this invention to provide a specific catalytic mechanism for the employment of the zinc salt compounds in various solvent systems employing unsaturated aldehydes and oxygen as reactants.

These and other objects and advantages of this invention will become apparent from the description of the invention which follows and from the claims.

DESCRIPTION OF THE INVENTION

According to the invention a process has been discovered in which α,β-unsaturated aliphatic acids are prepared by the liquid phase oxidation of the corresponding α, β-unsaturated aliphatic aldehydes and an in situ conversion or decomposition of corresponding peroxy (peroxide) compounds which are formed as a result of the oxidation reaction. The oxidation reaction is carried out at suitable temperatures and pressures in a suitable inert solvent in the presence of and under the catalytic effect of an organic or inorganic zinc salt compound.

When unsaturated aliphatic aldehydes, such as methacrolein, are oxidized in the liquid phase with oxygen or an oxygen-contaning gas, a mixture of products is obtained in the oxidate reaction product. The oxidate will generally contain some unreacted aldehyde, some of the corresponding peroxy (peroxide) compunds of the unsaturated aldehyde feed materials and the unsaturated acid product as well as the acid product and other by-products such as acetic acid. For example, the peroxy (peroxide) compounds co-produced in the autoxidation of methacrolein and crotonaldehyde would be permethacrylic acid and methacrolein monpermethacrylate and percrotonic acid and crotonaldehyde monopercrotonate respectively. Similar corresponding peroxy compounds would be produced with other unsaturated aldehydes such as acrolein, which may be employed in the process of this invention.

The preferred $\alpha,\beta$-unsaturated aliphatic aldehydes which may be employed as starting materials in this invention are the unsaturated lower aliphatic aldehydes, particularly the $\alpha,\beta$-unsaturated aldehydes having from 3 to 6 carbon atoms. Representative aldehydes include, for example, acrolein, methacrolein, ethacrolein, crotonaldehyde, alpha-chloroacrolein, 3-methycrotonaldehyde, 2-methylpentaldehyde and the like. Representative unsaturated acids produced by the process of this invention are, for example, acrylic acid, methacrylic acid and crotonic acid from acrolein, methacrolein and crotonaldehdye respectively.

The process of the invention may be carried out batchwise, semi-continuous or continuous in any suitable reactor such as a glass or aluminum reactor or autoclave. Although the order of addition of reactants and catalyst may vary somewhat, a general procedure is to charge the unsaturated aldehyde dissolved in a suitable solvent along with the catalyst into the reaction vessel which is equipped with a means for agitation of the liquid, and then introduce the proper amount of oxygen to the desired reaction pressure and heat the mixture if necessary to the desired temperature for the appropriate period. The reaction products are recovered and treated by any conventional method such as for example, by distillation, by extracting the acid with a base and subsequent acidification, or by solvent extraction.

Since the catalytic oxidation process of the present invention is a free radical reaction, it is desirable that apparatus unlikely to cause problems with such reaction mechanism be selected and any active sites which may be on the reactor surface and which may cause adverse catalytic activity under reaction conditions be passified or neutralized to render the surface essentially inert. Free radical reactions may be sensitive to the active material (active sites) of the reactor surface. Thus, the apparatus is preferably, for example, constructed of glass, titanium, polymeric materials such as polytetrafluorethylene (Teflon) or aluminum which desirably is treated by known methods for example, by washing the surfaces with hot hydrogen peroxide and/or with a sodium pyrophosphate solution or other chelating agents.

The catalytic zinc salt compounds or mixture of salt compounds which may be employed in the process of this invention for the liquid phase oxidation of $\alpha,\beta$-unsaturated aliphatic aldehydes including the in situ decomposition or conversion of the intermediate peroxy (peroxide) compounds formed during the autoxidation, to the corresponding $\alpha,\beta$-unsaturated aliphatic carboxylic acid may be an organic or inorganic zinc salt compound. Representative chemical forms of the zinc salt catalyst compounds which may be used as such or as mixtures or formed in the reaction system from the zinc metal are, for example, organic zinc compounds such as zinc acetate, zinc hexanoate, zinc acetylacetonate, zinc octoate, zinc formate, zinc lactate, ethyl sulfate linoleate, oleate, phenate, propionate, stearate, etc., and inorganic zinc salts compounds such as zinc carbonate, bromide, chloride, fluoride, hydroxide, sulfate, nitrate, iodide, oxide, etc. As indicated hereinabove, zinc metal per se may be added to the reaction, a zinc salt compound being formed in situ from at least a portion of the metal under reaction conditions, for example, zinc oxide.

The zinc salt compounds employed may be in a homogeneous state in the reaction mixture at reaction conditions. Thus, the compounds may be present in solution, or suspension and may also be on support materials which will not affect the reaction such as alumina, silica gel, aluminosilicates, activated carbon or zeolites. The compounds may be partially or completely soluble under reaction conditions and are preferably in a finely divided state. The reaction is carried out in the presence of a catalytic proportion of the zinc salt compound and will proceed with small amounts of the representative compounds hereinabove described. Generally the proportions of the zinc salt compound used in the reaction will be equivalent to between about 0.00001 to 0.5 mole and preferbly in amounts between about 0.001 to 0.01 mole of zinc salt compound per mole of the unsaturated aldehyde employed. In the absence of the catalytic quantities of the zinc salt compounds only a small amount of in situ decomposition or conversion of the intermediate peroxides to the unsaturated acid will occur.

The reaction is conducted in the liquid phase in which the unsaturated aliphatic aldehyde is generally dissolved in an inert organic solvent or mixture of solvents. The concentrations of unsaturated aldehyde in the mixture of solvents and aldehyde may be between about 5 percent and 90 percent and preferably between about 20 percent and 80 percent by weight of the aldehyde-solvent solution.

The solvents employed in the process of the invention must be inert under the reaction conditions used, i.e., non-reactive under the process conditions used, and preferably should be easily separable from the reaction mixture and components thereof including the aldehyde starting material, any intermediate products and acid product.

The solvents which may be employed in concentrations of from about 10 to 95 weight percent, preferably 20 to 80 weight percent of the solvent-aldehyde mixture and suitable for use in the process of the present invention can be aliphatic, cycloaliphatic and aromatic hydrocarbons and chlorinated hydrocarbons including halogenated aromatic hydrocarbons, carboxylic acids, ethers, esters and amides. Certain inert tertiary alcohols such as tertiary octyl alcohol, may also be employed. Representative solvents especially suitable for use in this invention include benzene, toluene, o-, m-, and p-xylenes, hexane, cyclohexane, ethylcyclohexane, chlorobenzene, bromobenzene, chlorotoluene, carbon tetrachloride, chloroform, methylene chloride, acetic acid, ethyl acetate, butyl acetate, methyl acetate, cyclohexyl acetate, methyl benzoate, tetrahydrofuran, dioxane, dimethylformamide, N,N'-dimethyl acetamide, etc. While solvents or mixtures of solvents are preferably employed in the process of this invention, some of the aldehydes which may be employed may be oxidized in the presence of catalytic amounts of the zinc salt compounds without the use of a solvent particularly if the zinc compound is essentially soluble in the liquid aldehyde.

The above solvents which may be employed in the process of the invention may also be mixed with water forming a heterogeneous solvent system. The water may amount to as low as about 5 percent or as much as 95 percent by weight of the reaction medium solvent solution and preferably ranges between bout 30 to 60 percent by weight of the total solvent solution employed. While water may possibly be used as the sole liquid component the essential purpose of employing a co-solvent, hydrocarbons, esters, etc., is to increase the solubility of the unsaturated aldehyde being employed.

The oxygen-containing gas employed in carrying out the oxidation process of the instant invention is generally oxygen itself or air. Air is included by the phrase "oxygen-containing gas" as are relatively pure oxygen gas and other oxygen-containing gases. Oxygen itself may be diluted with an inert gas such as nitrogen, carbon dioxide or helium.

The reaction is conducted at moderate temperatures, generally between 0° and 100° C. and preferably at temperatures of from about 20° to 80° C. and under sufficient pressure to maintain a liquid reaction phase. The reaction may be carried out at higher or lower temperatures with superatomspheric or subatmospheric pressures. The reaction may be carried out at atmospheric pressure and pressures of up to about 1500 psig may be employed. Elevated pressures of from about 50 psig to about 500 psig are particularly advantageous. When using an unsaturated aldehyde and/or solvent which may be relatively volatile, elevated pressures may be necessary to ensure reaction in the liquid phase.

Generally the reaction time may vary between a few minutes and several hours and is generally dependent on the aldehyde being reacted, temperature and pressure as well as the equipment being employed. Reaction times may vary dependent on whether the process is continuous or batch. The following examples are provided to illustrate the invention in accordance with the principles of this invention but are not to be construed as limiting the invention in any way except as indicated by the appended claims. Unless otherwise noted, percentages are in terms of percent by weight.

In the Examples which follow, except as specifically noted, a cylindrical aluminum reactor having a 45 ml. capacity was treated with a hot (80° C.) 30 percent solution of hydrogen peroxide, rinsed with acetone, dried in air and the aldehyde, the zinc salt catalyst and solvent charged to the reactor. The mixture was agitated by a magnetic stirring rod at the indicated reaction temperatures under oxygen pressure. Upon completion of the reaction, the mixture was cooled in a dry ice-isopropanol bath and the pressure slowly vented. To prevent polymerization of the reaction products, during recovery 0.1 g. of 2,6-di-tert-butyl-4-methylphenol was added.

The catalysts, solvents, reaction conditions and results are summarized in the following Table. Example 1 is a comparative example with no catalyst employed.

Analysis of the reaction product solutions were conducted as follows: A sample was titrated by differential potassium iodide to determine permethacrylic acid and methacrolein monopermethacrylate or other peroxide products produced as intermediate compounds during the autoxidation of aldehydes other than methacrolein. Another sample was reduced with triphenylphosphine and analyzed by gas-liquid chromatography to determine the aldehyde, carboxylic acid and other by-products such as acetic acid. A third sample was titrated by potassium hydroxide to determine total acidity.

In the Examples the following abbreviations are used:
MA — methacrolein
MAA — methacrylic acid
MMPM — methacrolein monopermethacrylate
PMAA — permethacrylic acid
$Zn(OHex)_2$ — zinc hexanoate
$Zn(C_2H_3O_2)_2$ — zinc acetate
$Zn(AcAc)_2$ — zinc acetylacetonate
$Zn(C_{18}H_{35}O_2)_2$ — zinc stearate
% MA Conv. — percent methacrolein conversion

TABLE

Autoxidation of Methacrolein — 30 per cent MA in Solvent

| Example | Catalyst | Solvent (g.) | Wt. % Conc. of Catalyst | MA (g) | Temp. °C. | $O_2$ Pressure (psig) | Time Min. | % MA Conv. | % Selectivity to MAA | PMAA | MMPM | Other By-Products[4] |
|---|---|---|---|---|---|---|---|---|---|---|---|---|
| 1 | none | n-hexane (4.50 g.) | — | 2.0 | 40 | 100 | 115 | 35 | 21 | 6 | 47 | 26 |
| 2 | $Zn(OHex)_2$ | n-hexane (4.50 g.) | 4.25[2] | 2.0 | 40 | 100 | 80 | 31 | 38 | 4 | 25 | 33 |
| 3 | $Zn(C_2H_3O_2)_2$ | n-hexane (4.50 g.) | 0.20 | 2.0 | 50 | 100 | 120 | 36 | 41 | 4 | 30 | 25 |
| 4 | $Zn(AcAc)_2$ | benzene (4.00 g.) | 0.16 | 2.0 | 45 | 200[5] | 130 | 35 | 42 | 4 | 30 | 24 |
| 5 | $Zn(NO_3)_2$ | dioxane (4.50 g.) | 0.25 | 2.0 | 60 | 100 | 80 | 30 | 40 | 2 | 33 | 25 |
| 6[1] | $Zn(C_{18}H_{35}O_2)_2$ | n-hexane (4.50 g.) | 0.58 | 2.0 | 35 | 100 | 150 | 32 | 45[3] | 2 | 28 | 25 |
| 7 | $ZnCl_2$ | dimethyl formamide (4.50 g.) | 0.30 | 2.0 | 50 | 100 | 120 | 31 | 38 | 4 | 32 | 26 |

[1] 2.0 g. acrolein employed as aldehyde — 30 per cent by weight in solvent.
[2] large excess of catalyst employed.
[3] acrylic acid product selectivity and corresponding peroxide compounds.
[4] includes acetic acid produced as by-product.
[5] 200 psig air employed instead of oxygen.

We claim:
1. A process for the liquid phase oxidation of an $\alpha,\beta$-unsaturated aliphatic aldehyde containing from 3 to 6 carbon atoms in an inert solvent solution to the corresponding unsaturated aliphatic carboxylic acid which comprises contacting said aldehyde with oxygen or an oxygen-containing gas at a temperature of from about

0° to 100° C. and a pressure between about atmospheric and 1500 psig in the presence of from about 0.00001 to 0.5 mole of a zinc salt catalyst selected from the group consisting of zinc nitrate, zinc chloride, zinc carbonate, zinc bromide, zinc fluoride, zinc hydroxide, zinc sulfate, zinc iodide and zinc oxide or mixtures thereof, per mole of said aldehyde to effect an in situ decomposition of intermediate peroxide compounds formed during the oxidation to said unsaturated aliphatic carboxylic acid.

2. A process according to claim 1 wherein the aldehyde is selected from the group consisting of acrolein and methacrolein.

3. A process according to claim 2 wherein the aldehyde is methacrolein.

4. A process according to claim 1 wherein the inert solvent is employed in concentrations of from about 10 to 95 weight percent of the solvent-aldehyde mixture and is selected from the group consisting of aliphatic, cycloaliphatic and aromatic hydrocarbons, carboxylic acids, ethers, esters and amides or mixtures thereof.

5. A process according to claim 4 wherein the concentration of solvent is from about 20 to 80 weight percent and said solvent is selected from the group consisting of n-hexane, benzene, dioxane and dimethylformamide.

6. A process according to claim 1 wherein the temperature is in the range of from about 20° to 80° C. and the pressure is between about 50 psig and 500 psig.

7. A process according to claim 1 wherein from about 0.001 to 0.01 mole of zinc salt catalyst per mole of aldehyde is employed.

8. A process according to claim 1 wherein air is employed as the oxygen-containing gas.

9. A process according to claim 1 wherein the zinc salt catalyst is supported.

10. A process for the liquid phase oxidation of methacrolein in an inert solvent solution to the corresponding methacrylic acid which comprises contacting said methacrolein with oxygen or an oxygen-containing gas at a temperature of from about 20° to 80° C. and a pressure of between about 50 psig and 500 psig in the presence of from about 0.001 to 0.01 mole of a zinc salt catalyst selected from the group consisting of zinc nitrate, zinc chloride, zinc carbonate, zinc bromide, zinc fluoride, zinc hydroxide, zinc sulfate, zinc iodide and zinc oxide or mixtures thereof, per mole of methacrolein to effect an in situ decomposition of intermediate permethacrylic acid and methacrolein monopermethacrylate formed during the oxidation to said methacrylic acid.

* * * * *